United States Patent [19]
Enzmann et al.

[11] Patent Number: 5,844,996
[45] Date of Patent: Dec. 1, 1998

[54] ACTIVE ELECTRONIC NOISE SUPPRESSION SYSTEM AND METHOD FOR REDUCING SNORING NOISE

[75] Inventors: Dieter Enzmann, Menlo Park; Anthony F. Matouk, Los Altos; Ahmet Karakasoglu, Palo Alto; Chin N. Hung, Santa Clara; James S. Abbott, San Francisco, all of Calif.

[73] Assignee: Sleep Solutions, Inc., Palo Alto, Calif.

[21] Appl. No.: 866,378

[22] Filed: May 30, 1997

Related U.S. Application Data

[63] Continuation of Ser. No. 728,768, Oct. 10, 1996, which is a continuation of Ser. No. 597,560, Feb. 2, 1996, which is a continuation of Ser. No. 206,464, Mar. 4, 1994, which is a continuation-in-part of Ser. No. 38,336, Feb. 4, 1993, abandoned.

[51] Int. Cl.$^6$ .................................................. A61F 11/06
[52] U.S. Cl. .......................................... 381/116; 381/71.11
[58] Field of Search .............................. 381/71, 94, 71.6, 381/71.7, 71.11, 71.12, 71.1, 72

[56] References Cited

U.S. PATENT DOCUMENTS

| | | |
|---|---|---|
| 4,153,815 | 5/1979 | Chaplin et al. ............................ 381/71 |
| 4,654,871 | 3/1987 | Chaplin . |
| 4,683,590 | 7/1987 | Miyoshi et al. .......................... 381/94 |
| 5,150,414 | 9/1992 | Ng .............................................. 381/71 |
| 5,224,168 | 6/1993 | Martinez et al. ......................... 381/71 |
| 5,381,485 | 1/1995 | Elliott ....................................... 381/71 |
| 5,386,689 | 2/1995 | Bozich et al. ............................. 381/71 |
| 5,427,102 | 6/1995 | Shimode et al. .......................... 381/71 |

FOREIGN PATENT DOCUMENTS

| | | |
|---|---|---|
| 168740A | 1/1986 | European Pat. Off. . |
| 3439-329A | 11/1985 | Germany . |
| 3719-974A | 12/1988 | Germany . |
| 4109312A | 8/1992 | Germany . |
| WO 87/02577 | 5/1987 | WIPO . |

OTHER PUBLICATIONS

*Adaptive Signal Processing*, Widrow & Stearns, Chapter 11, pp. 270–301, "Adaptive Control Systems", Prentice–Hall, Inc., Englewood Cliffs, NJ, 1985.

*Primary Examiner*—Curtis A. Kuntz
*Assistant Examiner*—Ping W. Lee
*Attorney, Agent, or Firm*—Flehr Hohbach Test Albritton & Herbert

[57] ABSTRACT

A system for attenuating noise which can be sensed by the auditory nerve comprising a microphone positioned in a first sound region for sensing noise present in the first sound region for creating a first electrical signal having a frequency and amplitude corresponding to the noise sensed in the first sound region. Circuitry is provided for processing the first electrical signal to create a second electrical signal having the same frequency but of opposite amplitude and sign of the first electrical signal. A speaker is provided for converting the second electrical signal to anti-noise for attenuation of the sensed noise in a second sound region spaced from the first sound region. A microphone is disposed in the second sound region for detecting any noise above a predetermined noise level in the second sound region to provide an error correction signal. Circuitry is provided responsive to the error correction signal to modify the second electrical signal to bring the noise in the second sound region so that it is below a predetermined noise level.

12 Claims, 9 Drawing Sheets

ACTIVE ELECTRONIC NOISE SUPPRESSION SYSTEM AND METHOD FOR REDUCING SNORING NOISE

This is a continuation of application Ser. No. 08/728,768 filed Oct. 10, 1996, which is a continuation of application Ser. No. 08/597,560 filed Feb. 2, 1996, which is a continuation of application Ser. No. 08/206,464 filed Mar. 4, 1994, which is a continuation-in-part of application Ser. No. 08/038,336 filed Feb. 4, 1993, now abandoned.

This invention relates to a system and method for cancelling involuntary noises from the airway of a human being and more in particular for the silencing of snoring noises and other involuntary noises emanating from the airway of a human being as well as environmental.

The sounds or noise of snoring in the human being originate in the airway of the human being and are generally believed to originate in the collapsible part of the airway where there is no rigid support which may involve the soft palate, uvula, tonsils, tonsillar pillars, base of the tongue, pharyngeal muscles and mucosa. The noise generated from these collapsible parts of the airway may be exacerbated by a restriction of airflow in the nasal passages, as for example through the nose which creates an increased negative pressure during inspiration which draws together the flaccid tissues in the collapsible part of the airway to cause them to vibrate and create the snoring noises. Snoring has also been defined as loud upper airway breathing, without apnea or hyperventilation, caused by vibration of the pharyngeal tissues. Heretofore many different types of apparatus and methods have been tried to stop the human being from snoring most of which have been relatively unsuccessful. Many of these approaches have been directed to devices which will cause the human being to assume positions in which the human being is less likely to snore. These also have been largely unsuccessful because they only slightly reduce the problem and often are of a great discomfort to the snorer and disturb the snorer's sleep. There is therefore need for a new and improved system and method which can overcome such problems.

In addition, there are many other noises which may affect the sleep of a human being. Of particular interest are non-repetitive or aperiodic environmental noises originating with transportation, such as trucks, buses, automobiles, motorcycles, airplanes, trains and the like, as well as noises associated with construction and manufacturing operations. There is therefore a need for a new and improved system and method which can address all of such noise sources. Also there are other environments in which ambient noise is troublesome such as in airplanes when using an airphone, in automobiles traveling on a freeway when using a car phone, in pay telephones when making a call and in many other situations when utilizing portable telephones.

In general, it is an object of the present invention to provide an active electronic noise suppression system and method which can be particularly useful against noise pollution and providing human beings with personal quietude.

Another object of the invention is to provide a system and method of the above character which is particularly effective with time varying aperiodic environmental noises.

Another object of the invention is to provide a system and method of the above character which is particularly applicable to observer or observer-side attenuation which can be defined as attenuation of noises in the vicinity of one's ears rather than creating a much larger quiet zone.

Another object of the invention is to provide a system and method of the above character for alleviating the problem of snoring by not attempting to cause the human to stop snoring, but by cancelling out such snoring by observer attenuation or cancellation.

Another object of the invention is to provide a system and method of the above character in which active noise cancellation is utilized by generating a sound wave which is of the same amplitude but of opposite sign to provide destructive interference of the noise wave form.

Another object of the invention is to provide a system and method of the above character in which a zone of silence or quietness is created in the vicinity of a bed partner or bedroom partner to provide observer cancellation or attenuation.

Another object of the invention is to provide a system and method of the above character which does not denigrate the sleep pattern of a snorer.

Another object of the invention is to provide a system and method of the above character for the elimination of noisy sounds of snoring thus allowing people that share a bedroom with a snorer to sleep restfully through the night.

Another object of the invention is to provide a system and method of the above character in which active noise control is utilized for cancelling such involuntary noises.

Another object of the invention is to provide a system and method of the above character which can be utilized to cancel noises from all forms of snoring including loud or exaggerated forms.

Another object of the invention is to provide a system and method of the above character in which the undesirable involuntary noises are cancelled by injection of an inverse sound wave.

Another object of the invention is to provide a system and method of the above character in which the inverse sound wave to be utilized can be predicted and then injected into the path of noise transmission for real-time performance.

Another object of the invention is to provide a system and method of the above character in which adaptive filtering is utilized for the active noise control in which the filtering is broad band rather than narrow band.

Another object of the invention is to provide a system and method of the above character in which an error signal is generated from the noise cancelled signal which is utilized with adaptive filtering to minimize new error.

Another object of the invention is to provide a system and method of the above character in which digital signal processing technology is utilized to generate the inverse sound wave.

Another object of the invention is to provide a system and method of the above character in which artificial neural networks are utilized for predicting and generating the inverse sound wave.

Additional objects and features of the invention will appear from the following description in which the preferred embodiments are set forth in detail in conjunction with the company drawings.

In general, the system for cancelling involuntary noises from the airway of a human being consists of at least one microphone or an input vibration sensor placed in relatively close proximity to the head of one bed partner to create an electrical signal representing the involuntary noises emanating from the human being. Means is provided for processing the electrical signal to create an inverse electrical signal. An error feedback microphone is provided near at least one of the ears of the other bed partner. At least one loudspeaker is utilized for converting the inverse electrical signal to a sound wave cancel the involuntary noises. The loudspeaker is positioned in the vicinity of the head of the other bed partner to create a local zone of silence around the ear of the other bed partner in which sound waves are substantially attenuated around the ear of the other bed partner for observer noise cancellation.

Figure 1:
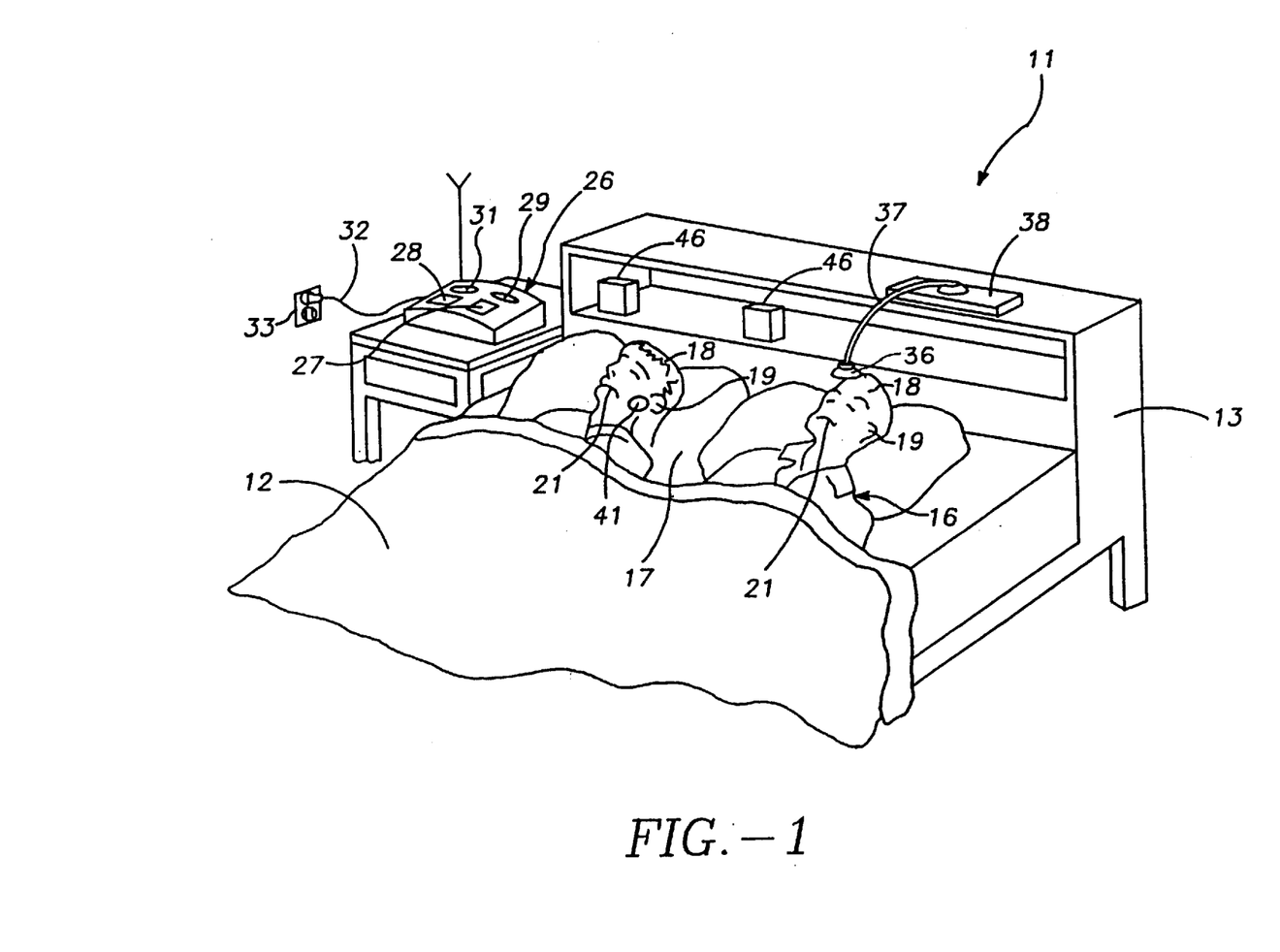
FIG. 1 is an isometric view of a system for cancelling involuntary noises from the airway of a human being showing its use in conjunction with a double bed in a bedroom in which one of the bed partners snores at least occasionally.

More in particular as shown in FIG. 1, the system 11 for cancelling involuntary noises from the airway of a human being is shown in use in a bedroom environment having a king size double bed 12 therein of a conventional type which is provided with a conventional headstand 13 and a nightstand 14 on at least one side of the bed 12. Bed partners or persons 16 and 17 are shown sleeping in the bed 12 and by way of example can be an older husband and wife in which the husband has a snoring problem. Each person 16 and 17 has a head 18 with ears 19 on opposite sides and a mouth 21.

A system 11 is provided for one of the bed partners and as shown consists of a control console 26 which by way of example can be placed on the nightstand 14. The control console 26 includes an on/off switch 27 and a reset switch 28 and green and yellow lights 29 and 31. The control console 26 is connected to a suitable source of power, as for example 110 volts 60 cycle AC through a power cord 32 connected to a conventional outlet 33.

The system 11 also includes at least one source microphone 36 to provide an electrical input to the system as hereinafter described. The microphone 26 is preferably mounted in close proximity and in a suitable manner about the head 18 of the snoring bed partner such as mounting it on the headstand 13 as shown in FIG. 1. The microphone 36 is positioned in such a manner so as to pick up involuntary noises emanating from the airway of the snoring bed partner through the mouth regardless of the position of the bed partner, whether the bed partner is lying on the right side, the left side or the back. The desired input signal can alternatively be obtained or picked up by using a vibration sensor (not shown) secured to the throat of the snoring bed partner or embedded in the pillow used by the snoring bed partner. Also, if desired, additional microphones (not shown) can be mounted in spaced-apart positions extending transversely of the head of the bed partner.

The microphone 36 as shown in FIG. 1 is carried by a flexible arm 37 of a conventional type secured to a mounting block 38 resting on the headstand 13. By using such a flexible arm 37, the microphone 36 can be placed in an optimum position by the snoring bed partner before going to sleep so that sleeping habits (i.e. lying on the back or one side or both sides) of the snoring bed partner can be considered. The microphone 36 may also be of the directional type, thus when three are used a three-dimensional configurations of placement about the snorer's head can be achieved. Thus, a central microphone overlies the head of the snoring partner and the other two microphones are disposed in spaced-apart positions on opposite sides of the same and can be moved into positions which are closer to the mouth and nose of the snoring partner to ensure that the microphones will pick the involuntary and objectionable noises emanating from the snoring partner in a first sound region as soon as possible.

It should be appreciated that the microphone 36 can be of the wireless type and can be provided with a clip permitting it to be attached in a desired location, as for example to a lapel of pajamas worn by the snoring partner.

At least one error microphone 41 is provided adjacent one ear 19 of the non-snoring partner. Preferably, one of the error microphones 41 is provided on each of the opposite ears 19 of the non-snoring partner 18. The error microphones 41 are of a self-contained type, and thus can be wireless or, if desired, can be connected by a conductor into the controller or control console 26.

At least one loudspeaker 46 and preferably multiple loudspeakers 46, as for example two loudspeakers 46 are provided for the other or non-snoring partner to provide observer noise cancellation or attenuation and are connected into the control console 26 by cables (not shown). As shown in FIG. 1 the loudspeakers 46 are mounted on the headstand 13 so they are in close proximity to the head 18 of the other or non-snoring bed partner 18 and preferably are positioned on opposite sides of the head of the partner 18 to create a local zone of silence or quietness adjacent the ears 19 of the non-snorer. These loudspeakers 46 can be wireless so as to allow a wide variety of three-dimensional configurations about a human head.

Figures 2, 3:
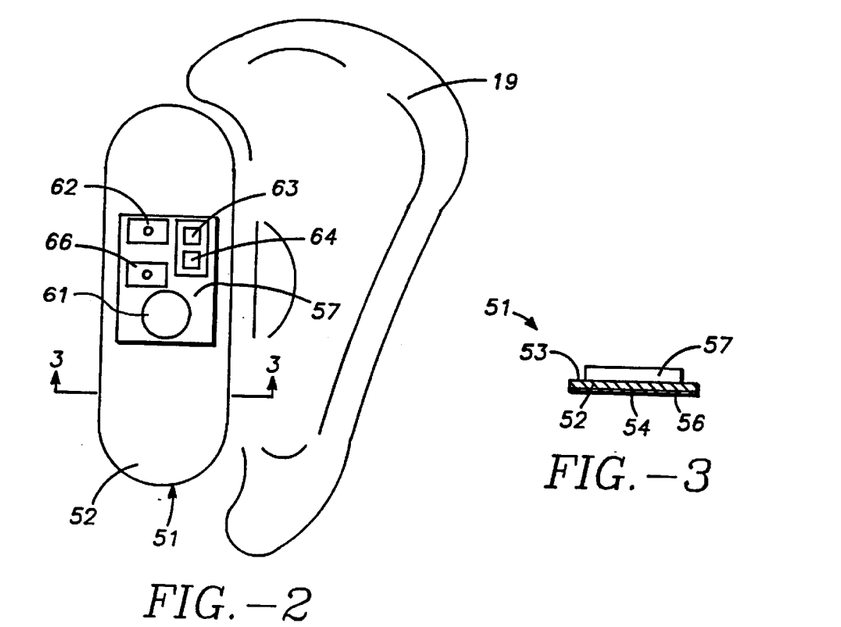
FIG. 2 is a side elevational view of a head a human wearing a band-aid type patch carrying a transmitter incorporating the present invention.
FIG. 3 is a cross-sectional view taken along the line 3—3 of FIG. 2.
Figure 4:
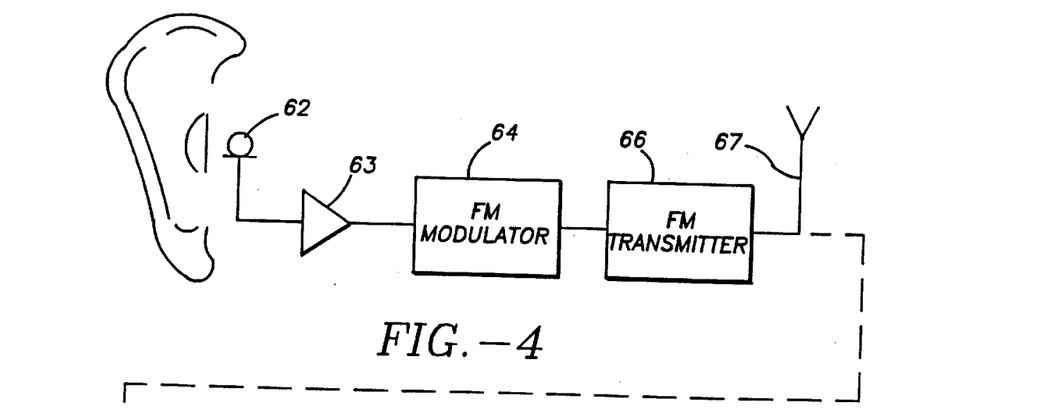
FIG. 4 is a block diagram of the transmitter shown in FIG. 2.
Figure 5:
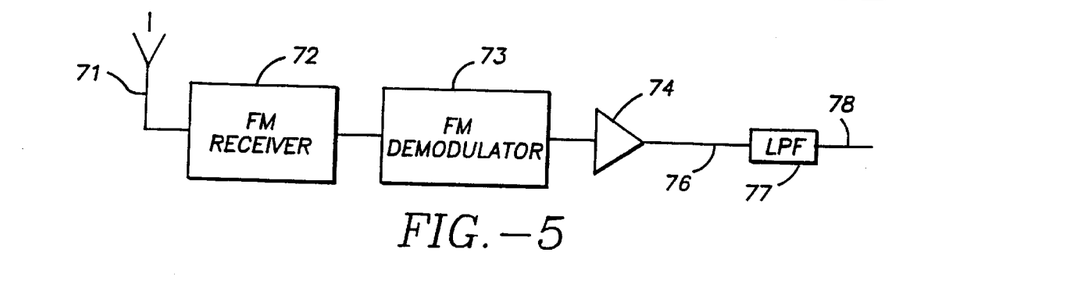
FIG. 5 is a block diagram of a receiver utilized in the system of the present invention.

The error microphone 41 is carried by a removable patch 51 as shown in FIGS. 2 and 3. The removable patch consists of a flexible plastic layer 52 having an elongate configuration with rounded ends. For example, it can be in the shape of a "band-aid" and has a length, as for example, of 1 to 1.5 inches so that it can be disposed in close proximity to the ear 19. The layer 52 is provided with first and second surfaces 53 and 54. An adhesive layer 56 is provided on the surface 54, and is of a conventional type and is of a type which can adhere to the skin of the patient, be removed and then replaced and removed repeatedly. A miniature printed circuit board 57 is provided on the first surface 53 and carries a battery 61. The battery is connected to a microphone 62 which is connected through pre-amp circuitry 63 through an FM modulator 64 to an FM transmitter 66, which supplies its output to an FM antenna 67. Such frequency modulating circuitry is well known to those skilled in the art, and typically can be used for transmitting at a desired frequency. The signal from transmitter antenna 67 is picked by a receiver antenna 71 mounted on the control console 26, which includes therein the circuitry which is shown in block diagram in FIG. 5. The signal which is received by the FM antenna 71 is supplied through a conventional FM receiver 72 to an FM demodulator 73 which supplies its output through an amplifier 74 to provide an error signal on line 76 which passes through a low-pass filter 77. This filtered error signal is supplied on a line 78.

Figure 6:
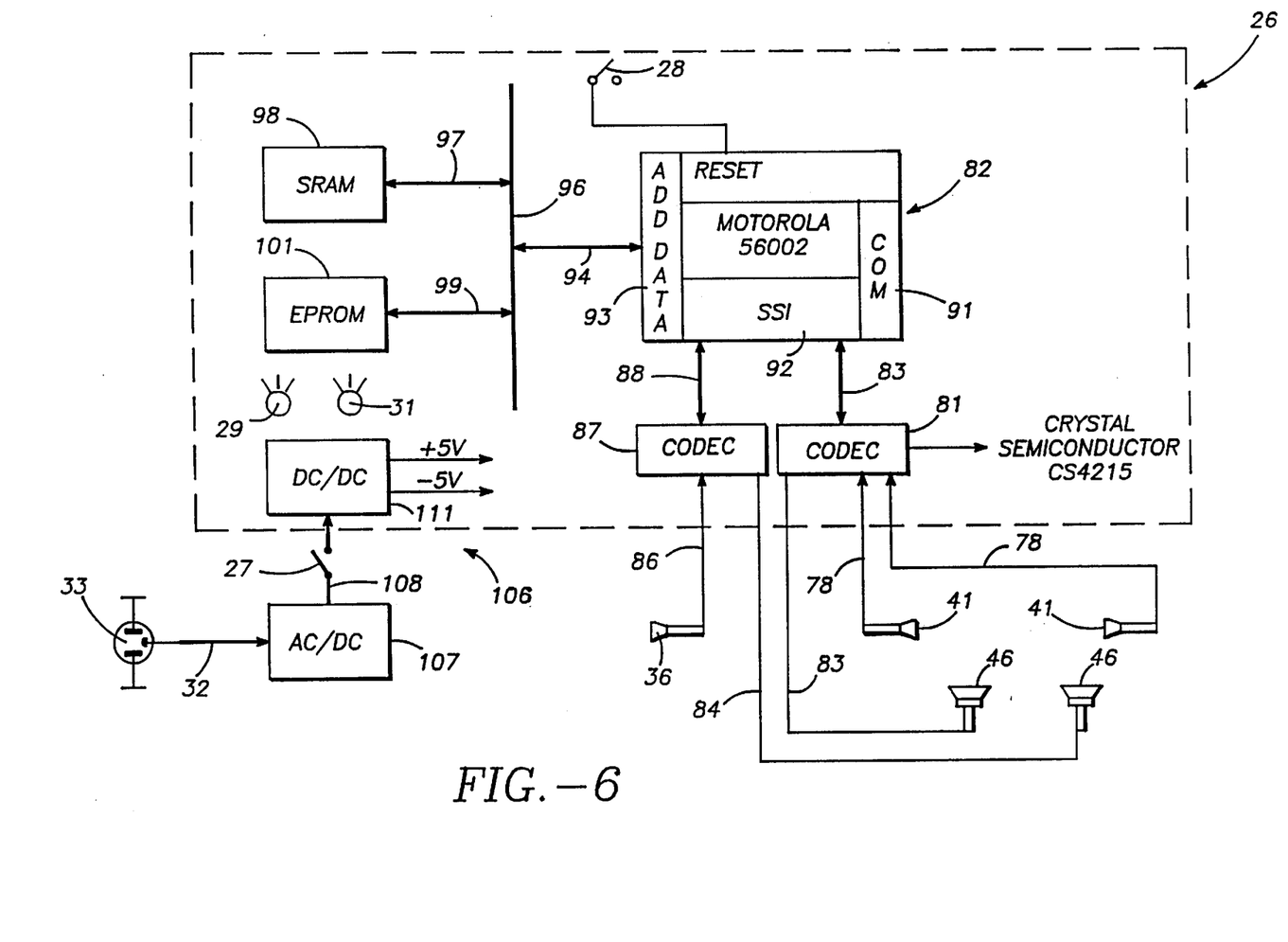
FIG. 6 is a block diagram of an active noise control system incorporating the present invention.

As shown in the block diagram in FIG. 6, the output from the error microphone 41 is supplied through the line 78 into circuitry which is contained within the control console 26 to a codec chip 81 of a conventional type. For example, the codec chip can be a CS4215, supplied by Crystal Semiconductor Corporation of Austin, Tex. 78760, audio chip with stereo analog-to-digital and digital-to-analog converters utilizing delta-sigma inversion techniques. It has a greater than 60 dB signal-to-noise ratio. It is provided with a programmable attenuation for the analog inputs and is provided with on-chip anti-aliasing filters. It is also provided with on-chip output smoothing filters. It also has a serial digital interface so that it can interface with a digital signal processor chip 82 through an interconnect 83. The codec chip 81 also has connected to the same the two speakers 46 which are by lines 83 and 84.

The source microphone 36 is connected by a line 86 to another codec chip 87 of the same type as codec 81, and is connected through an interconnect 88 to the digital signal processor 82. The digital signal processor 82 can be of a conventional type such as a Motorola 56002 chip. Such a chip is provided with communication ports 91 identified as COM in FIG. 6. It is also provided with a synchronized serial interface 92 identified in SSI. The chip 82 is also provided with address and data bus capabilities 93 identified as ADD DATA. The address and data capabilities 93 are connected by an interconnect bus 99 to a cross bus 96. The cross bus 96 is connected to an interconnect bus 97 to a static random access memory 98 identified as SRAM. The SRAM 98 has a suitable memory, as for example 64K×24 bits of memory. Similarly, the cross bus 96 is connected by an interconnect bus 99 to an erasable programmable read-only memory 101 identified as EPROM. The EPROM 101 has a suitable memory such as 32K×24 bits of memory.

The circuitry which is shown in block form in FIG. 6 and provided within the control console 26 is provided with a suitable power supply 106 which is connected to the power cord 32 connected to the outlet 33. The power supply 106 consists of an AC-to-DC converter 107 which converts 110 volts AC to 12 volts DC. The 12 volts DC is supplied on a line 108 through the on/off switch 27 to a DC-to-DC converter 111 which converts the 12 volts DC to +5 volts and −5 volts DC, which is supplied to various components of the circuitry, as shown in FIG. 6, in a conventional manner. A reset switch 28 is provided which is connected into the chip 82 for performing a reset function as hereinafter described.

Figure 7:
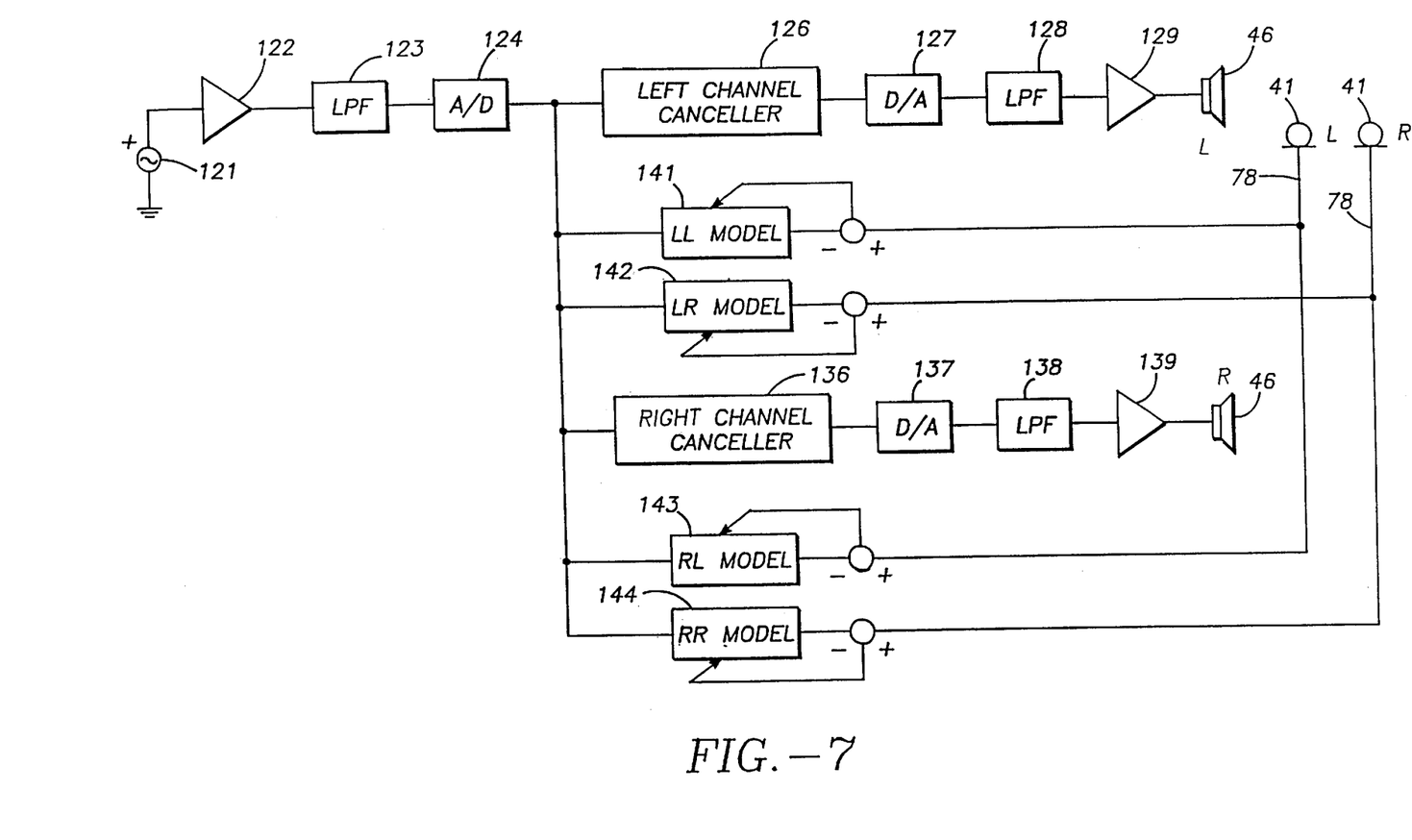
FIG. 7 is a block diagram showing the manner in which multi-channel modeling is accomplished with the circuitry shown in FIG. 6.
Figure 8:
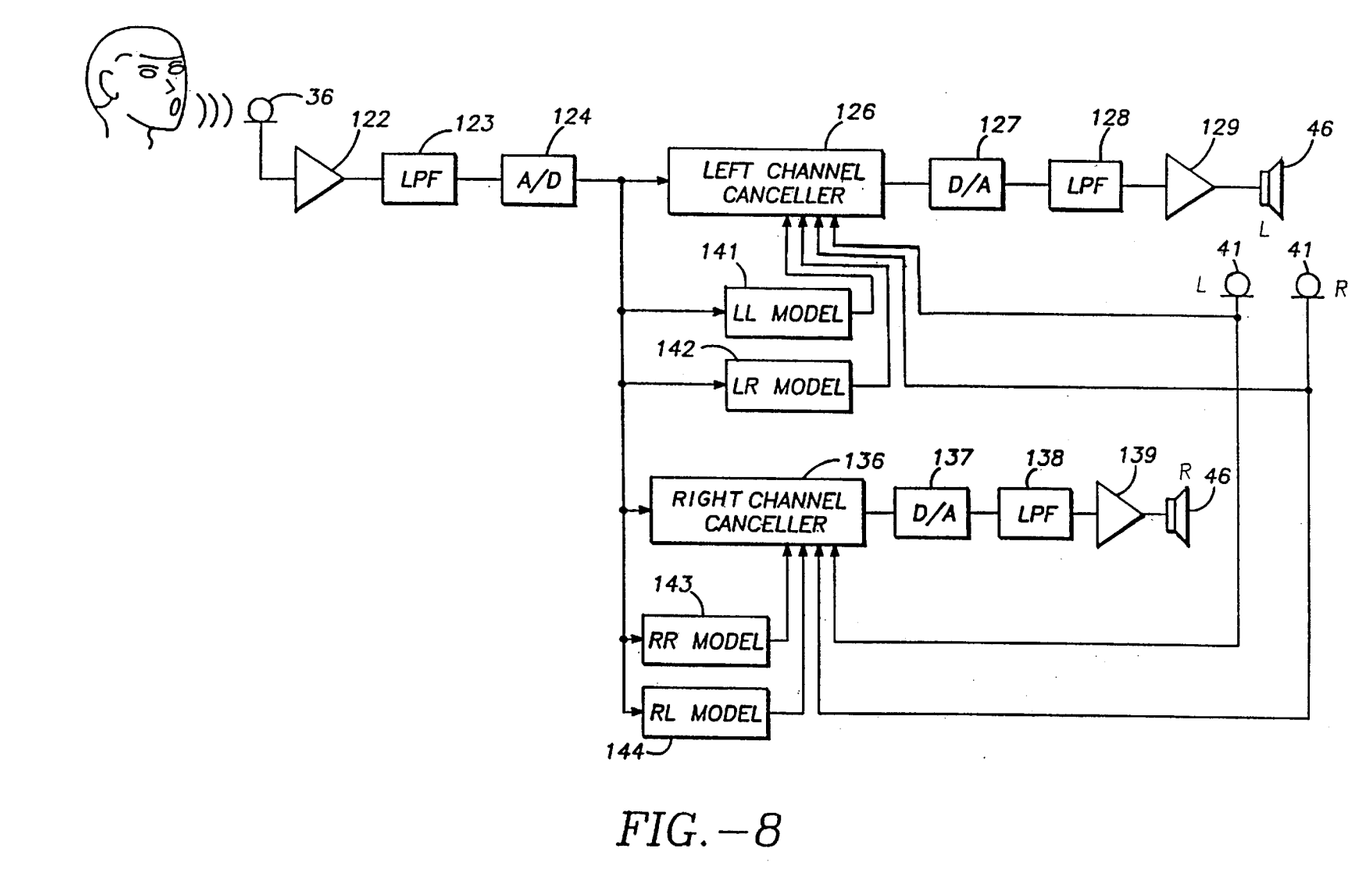
FIG. 8 is a block diagram showing the manner in which multi-channel cancellation is carried out in the apparatus shown in FIG. 6.

The operation of the circuitry which is shown in FIG. 6 in connection with the present invention can be best explained by the block diagrams in FIGS. 7 and 8, in which FIG. 7 depicts the multi-channel modeling which occurs using a modeling noise source 121, whereas FIG. 8 shows the multi-channel cancellation which occurs utilizing the circuitry of the present invention.

The software which is utilized in connection with the multi-channel modeling and the multi-channel cancellation is stored into the SRAM 98 and in the EPROM 101 so that the information is accessible to the digital signal processor chip 82.

Before noise cancellation can be undertaken, it is necessary to learn the transfer function between the various elements of the system as well as the room acoustics which can be characterized as white noise. Thus, for a system of the type as shown in FIG. 6, in which there are two error microphones 41 and two anti-noise speakers 46, there are four different transfer functions. Thus, there is one transfer function from the left anti-noise speaker 46 to the left error microphone 41, another transfer function from the left anti-noise speaker 46 to the right error microphone 41, and similarly a transfer function from the right anti-noise speaker 46 to the left error microphone 41, and another transfer function from the right anti-noise speaker 46 to the right microphone 41. These transfer functions versus frequency are utilized in connection with the software stored in the SRAM and the EPROM for creating multiple-input, multiple-output, multiple-error adaptive feed-forward control utilizing filtered-X normalized, least-mean-square (LMS) algorithms in adaptive filtering. Typically, to maintain optimal cancellation performance and stability of the system, the filtered-X LMS algorithm requires knowledge of the statistics of the input data in order to choose a proper algorithm step size. By utilizing a data-normalized, adaptive algorithm, it is possible to converge to a step-size range that is independent of the data statistics. For that reason the algorithm does not require prior knowledge of the input data for its use. Such an adaptive algorithm is not set forth in connection with the present disclosure because it is available from presently published literature. For example, see Chapter 11, pages 270–301 of a book entitled, "Adaptive Signal Processing" by Bernard Widrow and Samuel D. Stearns, published by Prentice-Hall, Inc., Englewood Cliffs, N.J. 07632, Copyright 1985, and also see a book entitled, "Active Control of Sound" by P. A. Nelson and S. J. Elliott published by Academic Press Copyright 1992, and a paper entitled, "Analysis of the Multiple Error and Block Least Mean Square Adaptive Algorithms" by Scott C. Douglas, submitted in June 1993 and accepted for publication in *IEEE Transactions on Circuits and Systems*, in "II: Analog and Digital Signal Processing." The multi-channel modeling is carried out as shown in FIG. 7 utilizing the modeling noise source 121, which can be white noise within the room itself or can be the noise from the snorer. This noise from the source 121 is supplied through an amplifier 122 through a low-pass filter 123 to an A/D converter 124. The output from the A/D converter 124 is applied to the left channel canceller 126 to a digital/analog converter 127 through a low-pass filter 128 and an amplifier 129 to the left noise suppression speaker 46. Similarly, the output from the A/D converter 124 is supplied to the right channel canceller 136 through a D/A converter 137 through a low-pass filter 138 and an amplifier 139 to the right noise suppression speaker 46. These outputs from the left and right speakers 46 are picked up by the left and right error microphones 41 which have their outputs connected to an LL model filter 141, an LR model filter 142, an RL model filter 143, and an RR model filter 144, representing the four transfer functions hereinbefore described, through summers 146 which provide feedback signals to the filters 141–144 through a feedback loop 147 as shown in FIG. 7. As also shown in FIG. 7, the filters 141–144 are also supplied with the output from the A/D converter 124.

The circuitry continues to operate until the outputs from the modeling circuits 141–144 converge to zero, or are sufficiently minimized. Typically, this can be accomplished in 10 seconds or less for each channel. As soon as the modeling has been completed, the circuitry can be utilized for noise cancellation as shown in FIG. 8.

As can be seen from FIG. 8, the circuitry in FIG. 8 is very similar to that shown in FIG. 7 with the exception that the outputs from the left and right error microphones 41 are supplied directly to the left and right channel cancellers 126 and 136, and the outputs from the LL model filter 141 and the LR model filter 142 are supplied to the left channel canceller 126 and the outputs from the RR model filter 143 and the RL model filter 144 are supplied to the right channel canceller 136. During multi-channel cancellation, the noise source is the microphone 36 which is positioned above the airway of the snorer, as shown in FIG. 1. The previously learned information during the multi-channel modeling is supplied by the model filters 141–144 to the appropriate left channel and right channel cancellers 126 and 136 to generate anti-noise by the left and right speakers 46 positioned on the opposite sides of the non-snoring bed partner 17 as shown in FIG. 1 to create a small zone of silence or quietness about the ears 19 of the non-snoring bed partner.

The error feedback microphones 41 will detect whether or not there is a zone of quietness about the ears 18 of the non-snoring bed partner. If for some reason the noise suppression speakers 46 do not provide a zone of quietness around the ears, the left and right microphones 41 immediately detect the same. This, for example, could occur because the snoring pattern of the snoring partner changes. As soon as this is sensed, the circuitry will go into the multi-channel modeling phase hereinbefore described until a convergence is achieved to again achieve substantially zero or small error signal or a minimum error signal, after which multi-channel cancellation can again proceed. Similarly, if the non-snoring partner 17 should shift his or her position while sleeping, which is enough to effect the transfer functions hereinbefore described, an error signal will be detected and the circuitry will go into the multi-channel modeling phase until a convergence at or near zero is reached within a predetermined time, which, by way of example as given earlier, should be less than 20 seconds, after which multi-channel noise cancellation can again occur.

With such a system, it can be seen that the system can be turned on at any appropriate time, as for example by the non-snoring bed partner 17 by having the non-snoring bed partner apply the removable patch 51 to each ear as shown in FIGS. 1 and 2, and then, upon entering the bed, turning on the system by turning the on/off switch 27 to the "on" position in the control console 26. When the non-snoring bed partner has assumed a relatively stable reclining position in the bed, the system will go through the multi-channel modeling procedure hereinbefore described, followed by the multi-channel cancellation.

If the non-snoring bed partner 17 awakes during the night and needs to leave the bed, as for example for going to the bathroom, the non-snoring partner can turn the system off by turning the on/off switch 27 to the "off" position. Alternatively, the non-snoring partner can do nothing, and go to the bathroom, and when returning can enter the bed and press the "reset" button or switch 116 to initiate the multi-channel modeling procedure hereinbefore described, which is followed by a multi-channel cancellation.

Upon arising in the morning, the non-snoring bed partner can turn the system off by turning the on/off switch 27 to the "off" position the removable patches 21 can be removed and placed in the nightstand 14 so that they are ready for use the following evening.

Figure 9:
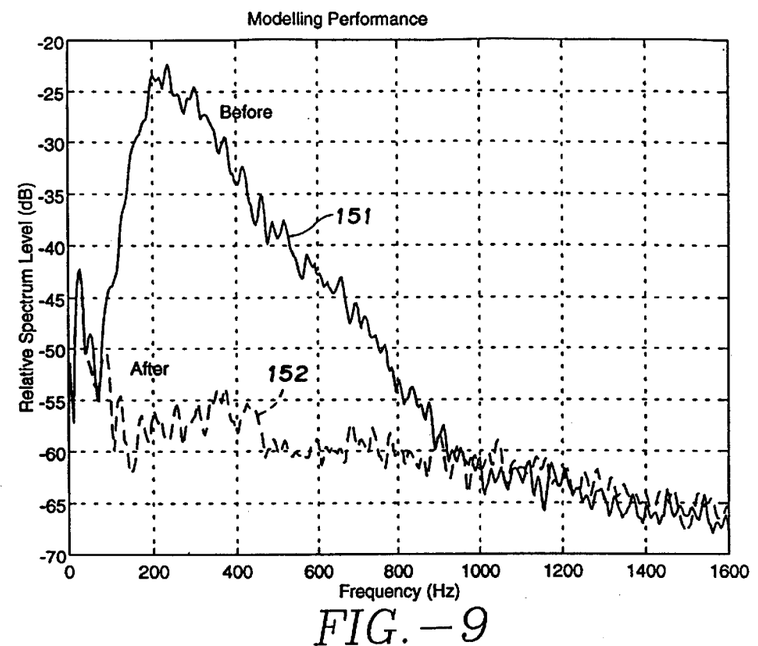
FIG. 9 is a graph showing the modeling performance for the apparatus shown in FIG. 6.
Figure 10:
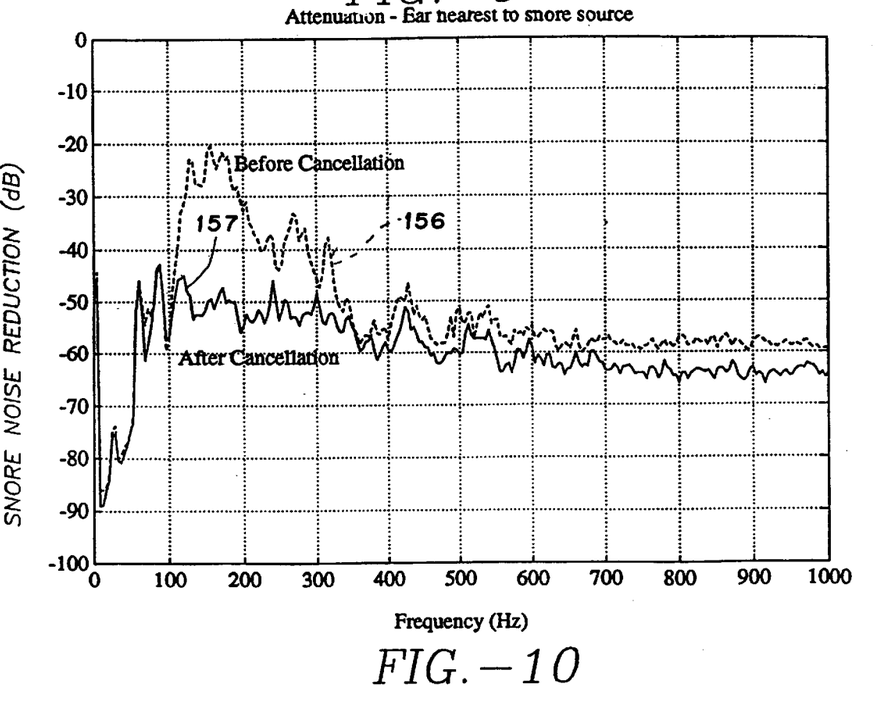
FIG. 10 is a graph showing the multi-cancellation occurring in the apparatus shown in FIG. 6.

The performance which can be achieved with a system incorporating the present invention is shown in FIGS. 9 and 10. FIG. 9 is a graph showing measured modeling performance of the system of the present invention, with the line 151 showing the performance before modeling and the broken line 152 showing the performance after modeling. The abscissa shows the error noise reduction (dB) from zero to −100 dB with respect to frequency on the ordinate in Hz from zero to 1000. From the graph it can be seen that there is at least 20 dB of attenuation between before modeling and after modeling in the low frequency range from zero to approximately 250 Hz, which is the most important region because this covers most of the snoring sounds typically generated by human beings. In general, it can be said that is desired to have at least 20 dB attenuation during the modeling.

The performance of the system 11 during noise cancellation is shown in FIG. 10, in which snore noise attenuation or reduction on the same scales as in FIG. 9 with broken line 156 representing the snore noise prior to cancellation and the line 157 shows the snore noise reduction or attenuation after cancellation provided by the system of the present invention.

From examination of the curves represented by the lines 156 and 157, it can be seen that there is approximately 30 dB of cancellation or noise suppression from peak to peak in the 150 Hz frequency range. It can be seen that the noise cancellation system attempts to bring the snoring noise level down to a line which is relatively flat and near the level of the ambient noise in the room.

In connection with the present invention, it is desirable that the system at least attenuate the snore noise by at least 20 dB or greater.

In connection with generating the zone of silence or quietness in the system of the present invention, the zone of silence can be characterized as a spherical volume which has a diameter which is approximately 1/10 of the wavelength of the frequency to be attenuated. Thus, by way of example in the present invention, in which it is desired to attenuate sounds from 100 Hz to 1.0 kHz, thus, typically, the wavelength would be from 3.4 m to 34 cm, and 1/10 of this provides a zone of silence in the vicinity of approximately two inches in diameter, which is a large enough volume of silence to cover the outlines of the human ear. This is particularly satisfactory for the snoring noises which have frequencies most, if not all of which, are below 400 Hz. Thus, where the system is to be utilized for attenuating snoring sounds, there is very little need for good performance at high frequencies. Therefore providing performance at 1.4 kHz and below provides excellent sound coverage for snoring sounds.

By providing the removable patches 51 for the ears, it is possible to provide microphones near the ear where they can be worn comfortably and unobtrusively. The anti-noise speakers are spaced from the ear and thus do not interfere with movement of the head of the person wearing the microphones. In addition, it is possible for the person wearing the microphones to hear other sounds which it may be desirable to hear, as for example fire alarms, a telephone ringing, and the like. The system is also advantageous in that it does not require the wearing of headsets over the ears.

In connection with the foregoing system, the digital signal processor 82 utilizes a neural network in performing the left and right channel cancellations as set forth by the blocks 126 and 127 in FIGS. 7 and 8, which, as well known to those skilled in the art, have the capability of being trained to learn and predict to provide a substantial real-time response to provide the necessary reverse amplitude signals in real time to achieve the noise cancellation or attenuation hereinbefore described.

Although the system of the present invention has utilized a digital neural network to achieve the desired results, it should be appreciated that if desired, an analog neural network also can be utilized to achieve the same purpose, the main difference being that the processing in the system takes place in an analog format rather than in a digital format.

The artificial neural network utilized in the present invention has the capability of learning to recognize new patterns, which is an important characteristic in the handling of the variability occurring with snoring and other similar noise patterns. The artificial neural network has parameters that control how they learn as they cycle repeatedly through the training data. The values selected for these parameters influence how well the training network performs. The key to the learning algorithm is its ability to change the values of its weights in response to errors. For it to able to calculate the errors, the training data must contain a series of input patterns labeled with their targeted output patterns. During training, the network passes each input pattern through the hidden layer to generate a result at each output node. It then subtracts the actual result from the target result to find the output layer errors. Next, the network passes the derivatives of output errors back to the hidden layer, using the original weighting correction. Each hidden node then calculates the weighted sum of the errors to find its indirect contribution to the known output errors. After each output in a hidden node finds its error value, the node adjusts its weight to reduce its error. The equation that changes the weights is designed to minimize the sum of the network's squared errors.

It should be appreciated that a neural network also can be readily trained to differentiate between desired sounds, such as from the telephone, a fire alarm or a front doorbell, as distinguished from undesirable sounds such as snoring.

Figure 11:
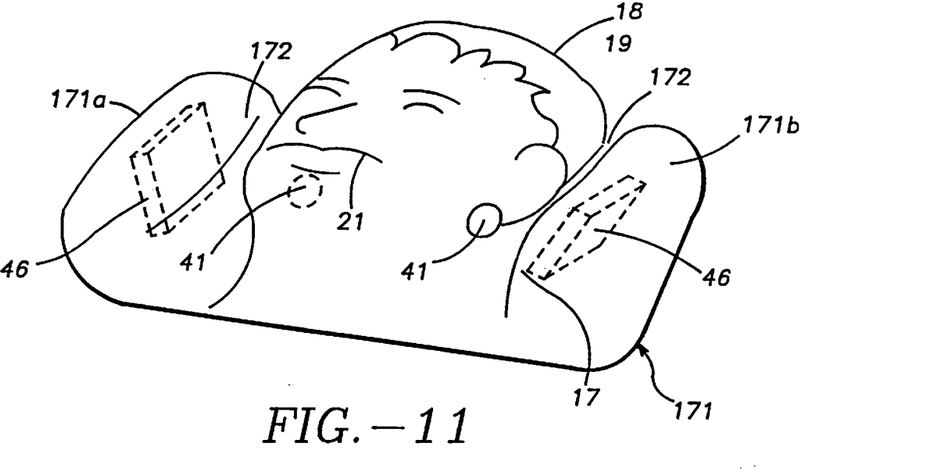
FIG. 11 is a partial isometric view showing a pillow-type arrangement for use in the system.

In FIG. 11, there is shown a pillow concept utilizing the system 11 of the present invention. In this embodiment of the invention, it can be seen that the two noise suppression speakers 46 are embedded within the outer confines of a pillow 171 having a generally U-shaped configuration with side portions 171a and 171b having outer surfaces 172 which are space apart outwardly from the ears 19 and are generally substantially vertically disposed so that the speakers 46 carried within the interior thereof are facing in the direction of the ears 19. A pillow 71 having this configuration would also provide a more attractive bedroom environment. The pillow is shaped in such a manner so that the user can still move his or her head in the pillow, and even permit the person utilizing the same to sleep on one or the other sides.

Figure 12:
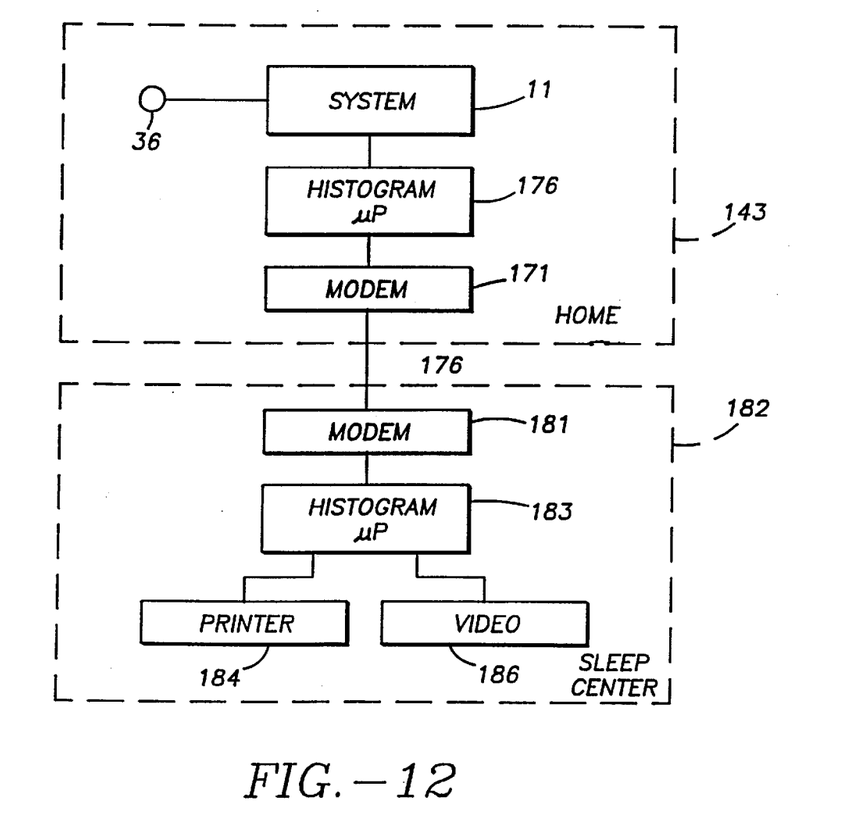
FIG. 12 is a block diagram showing an artificial neural network of the present invention being utilized in conjunction with a patient and a sleep center.

The system 11 of the present invention can be utilized for monitoring the sleep of a patient. Thus as shown in FIG. 12, the system 11 can be connected to a microprocessor 176 provided in the home, which would generate a histogram of the snoring being picked up by the microphone 36. The histogram generated by the microprocessor can be sent over a modem 171 provided in the patient's home over a communication link 178 of a suitable type such as a telephone line or a microwave link, from the patient's home 179 to a modem 181 provided in the doctor's office 182. The information from the modem 181 also can be supplied to a sleep center 182 which has a microprocessor 183 therein for converting the histogram information into human readable form, as for example by supplying it to a printer 184 or to a video terminal 186. In this way it is possible for a doctor in the sleep center to analyze the histogram to ascertain whether or not the snoring pattern is one which has manifestations which warrant medical treatment. This makes it possible to make such analysis without the doctor visiting the home of the patient or, alternatively, having the patient sleep in the sleep center.

Figure 13:
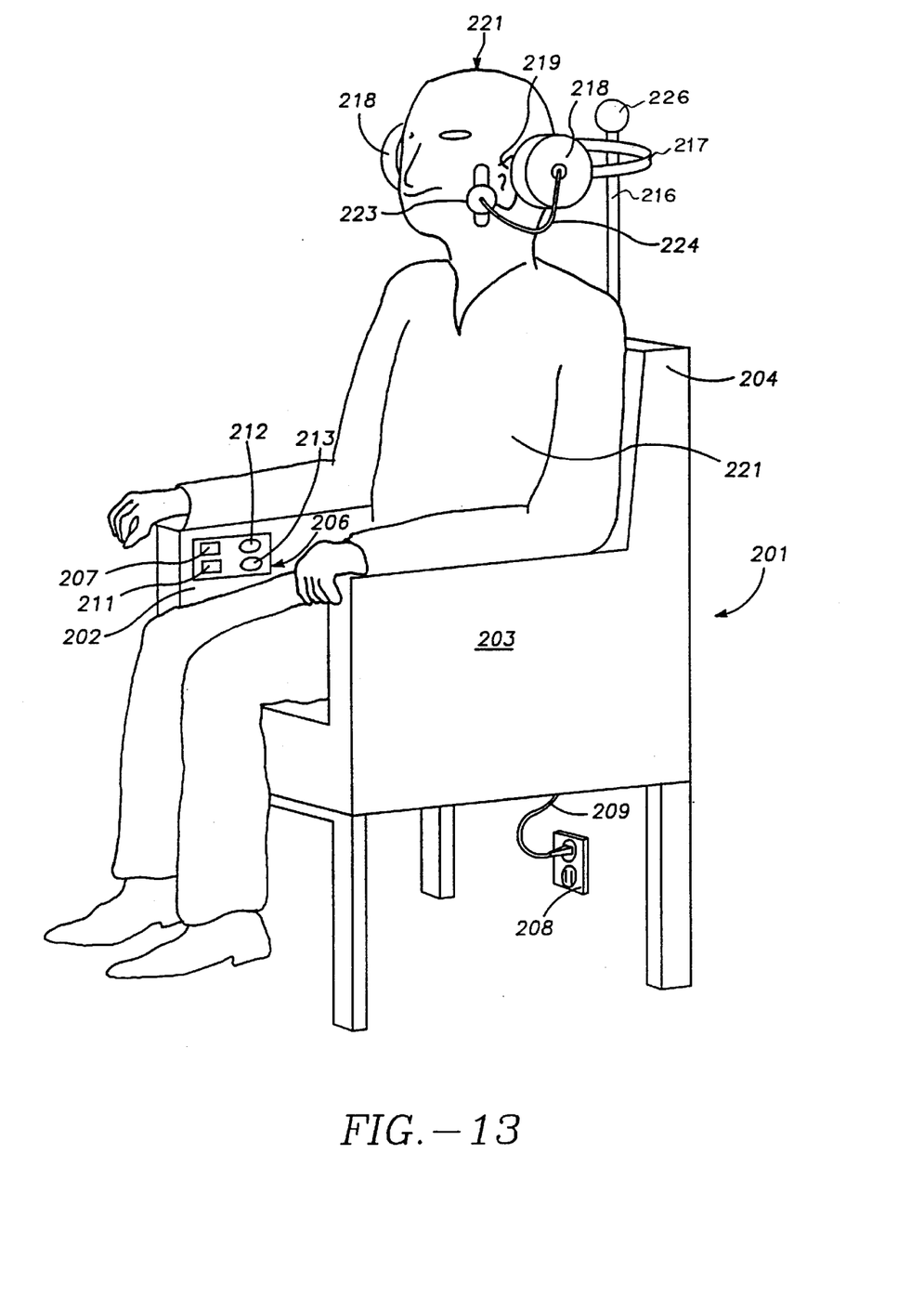
FIG. 13 is an isometric view showing the apparatus of the present invention being utilized to provide environmental noise cancellation for a noisy environment, as for example a seat at an airport.

Another application for the system 11 incorporating the present invention is shown in FIG. 13, in which the system is being utilized to provide a zone of quietness in a noisy location, as for example at an airport. Thus, there is provided a chair or seat 201 of a conventional type located in an airport which is provided with first and second spaced apart arm rests 202 and 203 and a back 204. The electronics of the system hereinbefore described can be incorporated into one of the arm rests and a control panel 206 provided on the exterior of the arm rest 202 as shown in FIG. 13. The control panel 206 can be provided with an on/off switch 207 to control the application of power from a power receptacle 208 provided at the airport, and which is connected by a power cord 209 to the system 11 incorporated within the chair. The control panel 206 can also be provided with a reset switch 211 if that is desired, as well as lights 212 and 213 of the type hereinbefore described in conjunction with the control console 26.

As also shown in FIG. 13, the chair 201 can be provided with a vertically adjustable pole 216 which carries a U-shaped member 217. Two noise suppression speakers 218 are mounted on opposite extremities of the member 217 and are spaced apart at a height in line with the ears 219 of the user 221. Error detection microphones 223 of the type hereinbefore described are attached by the user in the vicinity of his ears 219 when he takes a seat in the chair 201. The microphones 223 are connected by cords 224 into the system of the present invention, rather than by use of the FM radio link hereinbefore described. A source microphone 226 for picking up local environmental noises is also mounted on the pole 216.

In such an embodiment, it can be seen that the user or person 221 sitting in the chair will have a zone of silence created around his ears so that airport noises which will be picked up by the source microphone 226 which can be located in an appropriate position as, for example, on the pole 216 or alternatively on an adjacent window of the airport in the vicinity of the chair 201. This makes it possible for the person using the chair to have quiet so he can read or carry on any other thinking processes or even possibly take the opportunity to sleep if that is desired. When the person no longer wishes to remain in the chair, it is merely necessary for him to turn the on/off switch 207 to off and to disconnect the error microphones 223 from his head.

Figure 14:
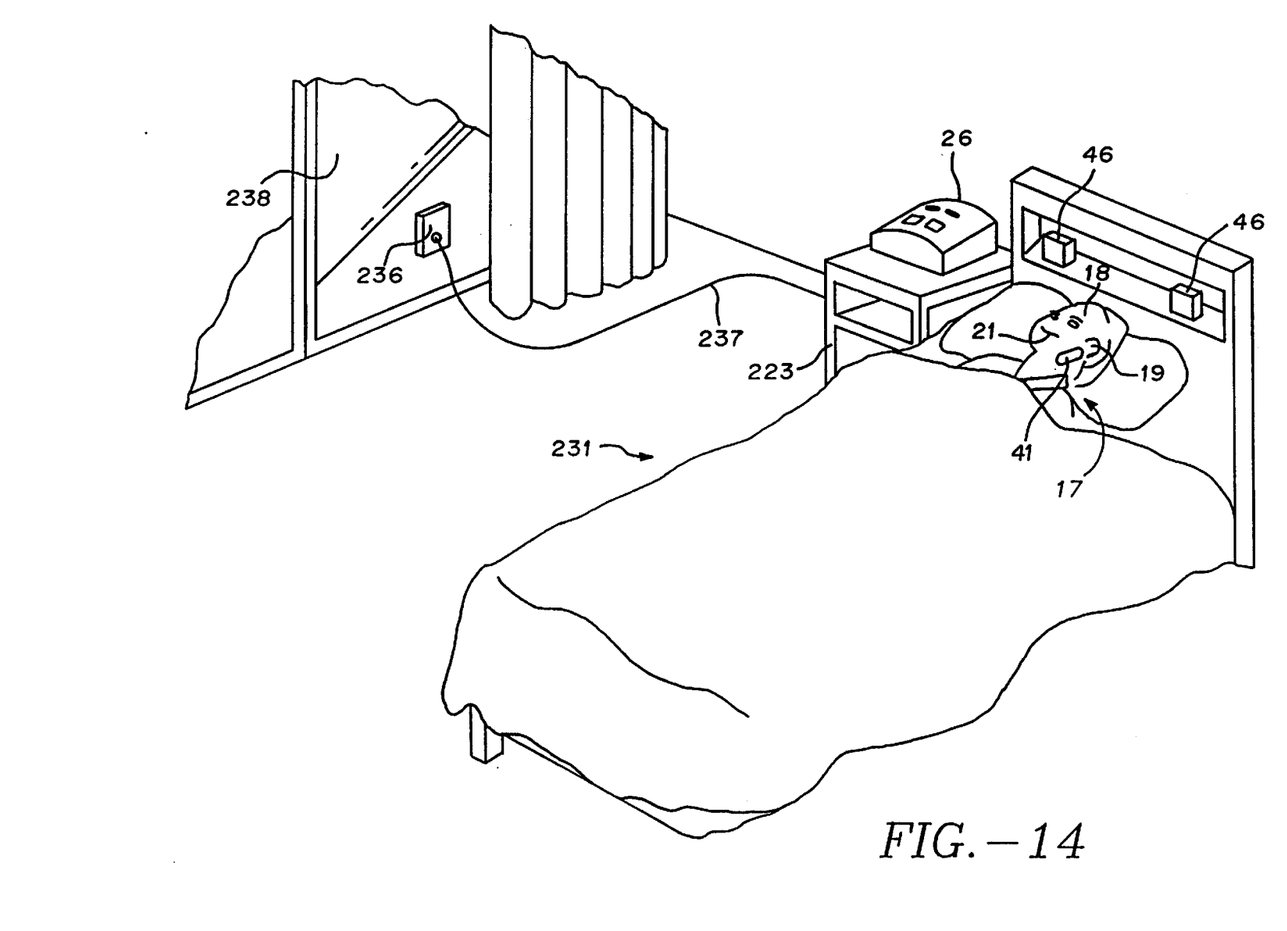
FIG. 14 is an isometric view showing the apparatus of the present being utilized for cancelling environmental noise in a bedroom.

Still another use of the system 11 is shown in FIG. 14, in which the system 11 is utilized for silencing environmental noise, as for example in a hotel room near an airport or train station. Thus, the person 17 is shown in a single bed 231 which is provided with a headboard 232 and a nightstand 233 which carries the control console 26.

In this embodiment of the invention, the source sensor, rather than being a microphone in the vicinity of the mouth of a snorer, would be a source sensor 236 connected by a cord 237 into the controller 26. The source sensor, by way of example, could be a vibration sensor placed on a sliding window 238. The system would operate in the same way to create a zone of silence around the ears of the person 17 sleeping in the bed, with the speakers 46 provided in the headboard generating the noise suppression and with the error microphones 41 picking up any error noise which may be present in the noise suppression created by the speakers 46. Thus, there is created a zone of silence or quietness around the ears of the user 17, making it possible for the user to sleep in a very noisy environment without difficulty. In addition to the vibration sensor 236, it should be appreciated that additional noise source sensors can be located in other parts of the room in which the person is sleeping, as for example near a doorway to cancel out noise from a hallway.

The system of the present invention can readily handle multiple channels of noise, thus making it possible to utilize a plurality of noise sensors.

What is claimed is:

1. A system for use by first and second human beings as bed partners lying in a bed for attenuating noise emanating from the airway of the first human being which can be sensed by the auditory nerves of the second human being, the second human being having a head with first and second ears comprising a modeling noise source, first electromechanical means positioned in a first sound region for sensing involuntary snoring noise emanating from the airway of the first human being for creating a first electrical signal having a frequency and amplitude corresponding to the snoring noise sensed in the first sound region, first electrical means for processing the first electrical signal to create a second electrical signal having the same frequency and opposite phase of the first electrical signal and second electromechanical means including first and second speakers in the vicinity of each of the ears of the second human being for converting the second electrical signal to anti-snoring noise for attenuation of the involuntary snoring noise emanating from the airway of the first human being and present in the vicinity of the ears of the second human being, third electromechanical means mounted on the head of the second human being and including a first error microphone located near the first ear and a second error microphone located near the second ear of the second human being for detecting any noise above a predetermined noise level in the vicinity of the first and second ears of the second human being to provide first and second error correction signals and means responsive to the first and second error correction signals to modify the second electrical signal to bring the involuntary snoring noise in the vicinity of the first and second ears of the second human being so that the involuntary snoring noise is below the predetermined noise level, said first electrical means including modeling means using the source of modeling noise for learning the four acoustical transfer of functions versus frequency between the first and second error microphones and the first and second speakers and producing modeling outputs and noise cancellation means utilizing the modeling outputs to generate anti-noise in the first and second speakers.

2. A system as in claim 1 wherein said processing means includes means for learning from the first electrical signal and predicting in real time a subsequent first electrical signal to create the second electrical signal.

3. A system as in claim 2 wherein said processing means includes means for ascertaining whether there is any error between the predicted first electrical signal and the actual first electrical signal, and means for making a correction in the first electrical signal in accordance with any error ascertained to thereby enhance the capability of predicting in real time a subsequent first electrical signal to be utilized in creating the second electrical signal.

4. A system as in claim 1 wherein said means for processing the first electrical signal to create a second electrical signal includes a variable phase network.

5. A system as in claim 1 wherein said means for processing the first electrical signal to create a second electrical signal includes an analog neural network.

6. A system as in claim 1 wherein said means for processing the first electrical signal to create a second electrical signal includes an A/D converter, a processor connected to the A/D converter and a D/A converter connected to the processor.

7. A system as in claim 6 wherein said processor is a digital signal processor.

8. A system as in claim 6 wherein said processor is a digital neural network.

9. A system as in claim 1 wherein said noise cancellation means includes first and second noise cancellers coupled respectively to the first and second speakers.

10. A method for attenuating involuntary snoring noise emanating from the airway of a first human being as a bed partner sleeping in a bed with a second human being as a second bed partner, the second human being having a head with first and second ears, comprising sensing in the vicinity of the airway of the first human being the involuntary snoring noise emanating from the airway of the first human being, creating a first electrical signal having a frequency and amplitude corresponding to the involuntary snoring noise, processing the first electrical signal to create a second electrical signal having the same frequency and opposite phase of the first electrical signal, converting the second electrical signal to anti-snoring noise to attenuate the involuntary snoring noise present at the first and second ears of the second human being, detecting in close proximity to the first and second ears of the second human being any involuntary snoring noise above a predetermined noise level to provide electrical error correction signals to modify the second electrical signal to bring the involuntary snoring noise present at the first and second ears of the second human being to a level so that it is below the predetermined noise level, said processing of the first electrical signal including utilizing a source of white noise to ascertain the acoustical transfer functions between the detecting in close proximity to the first and second ears of the second human being and the delivery of anti-snoring noise into the vicinity of the first and second ears of the second human being and utilizing the acoustical transfer of functions to generate anti-noise in the vicinity of the first and second ears of the second human being.

11. A method as in claim 10 wherein said processing step includes the steps of learning from the first electrical signals and predicting in real time a subsequent first electrical signal to create the second electrical signal.

12. A method as in claim 10 together with the steps of ascertaining whether there is any error between the predicted subsequent first electrical signal and the actual first electrical signal in making a correction in the first electrical signal in accordance with the error ascertained and thereby enhance the capability of predicting in real time a subsequent first electrical signal.

* * * * *

UNITED STATES PATENT AND TRADEMARK OFFICE
CERTIFICATE OF CORRECTION

PATENT NO. : 5,844,996
APPLICATION NO. : 08/866378
DATED : December 1, 1998
INVENTOR(S) : Dieter Enzmann et al.

It is certified that error appears in the above-identified patent and that said Letters Patent is hereby corrected as shown below:

Title page, item [75] inventor name is:
"James F. Abbott".

Signed and Sealed this

Twenty-second Day of December, 2009

David J. Kappos
*Director of the United States Patent and Trademark Office*